(12) United States Patent
Johnson

(10) Patent No.: US 11,259,480 B2
(45) Date of Patent: Mar. 1, 2022

(54) INBRED CORN LINE MDS2713

(71) Applicant: Masters Choice, Anna, IL (US)

(72) Inventor: Cullen Johnson, Anna, IL (US)

(73) Assignee: L & P Consulting, Anna, IL (US)

( * ) Notice: Subject to any disclaimer, the term of this patent is extended or adjusted under 35 U.S.C. 154(b) by 0 days.

(21) Appl. No.: 16/781,283

(22) Filed: Feb. 4, 2020

(65) Prior Publication Data

US 2020/0245580 A1  Aug. 6, 2020

Related U.S. Application Data

(60) Provisional application No. 62/800,889, filed on Feb. 4, 2019.

(51) Int. Cl.
*A01H 5/10* (2018.01)
*A01H 6/46* (2018.01)

(52) U.S. Cl.
CPC ............ *A01H 6/4684* (2018.05); *A01H 5/10* (2013.01)

(58) Field of Classification Search
None
See application file for complete search history.

(56) References Cited

U.S. PATENT DOCUMENTS

| 9,518,269 B2 * | 12/2016 | Schuetz | ............ C12N 15/8283 |
| 9,867,344 B2 * | 1/2018 | Kleinschmidt | .......... A01H 5/10 |
| 2020/0245579 A1 | 8/2020 | Johnson | |
| 2020/0245581 A1 | 8/2020 | Johnson | |

* cited by examiner

*Primary Examiner* — Medina A Ibrahim
(74) *Attorney, Agent, or Firm* — Armstrong Teasdale LLP

(57) ABSTRACT

An inbred corn line, designated MDS2713, is disclosed. The disclosure relates to the seeds of inbred corn line MDS2713, to the plants of inbred corn line MDS2713 and to methods for producing a corn plant, either inbred or hybrid, by crossing the inbred line MDS2713 with itself or with another corn line. The disclosure further relates to methods for producing other inbred corn lines derived from the inbred MDS2713.

18 Claims, No Drawings

INBRED CORN LINE MDS2713

This application claims the benefit of priority to U.S. Provisional Application Ser. No. 62/800,889, filed Feb. 4, 2019, the entire contents of which are hereby incorporated by reference herein.

FIELD OF THE DISCLOSURE

The present disclosure relates the field of corn breeding, in particular to a new and distinctive corn inbred line, designated MDS2713.

BACKGROUND OF THE DISCLOSURE

A major objective of commercial maize production is to produce high yielding, agronomically sound hybrid plants that perform well in selected growing regions. To produce these types of hybrids, inbreds may be developed which carry desired traits into the hybrid combination. Typically, hybrids are not uniformly adapted for all growing regions, but instead are specifically adapted for particular combinations of growing conditions associated with different growing regions. For example, Northern regions of the Corn Belt of the U.S. require shorter season hybrids than do southern regions of the Corn Belt. Hybrids that grow well in Colorado and Nebraska soils may not flourish in rich Illinois soil. Thus, a variety of major agronomic traits are selected to customize each hybrid combination for each particular growing region, and these selected agronomic traits impact hybrid performance.

Maize breeders select for a variety of inbred traits that impact the performance of a hybrid derived from the parental inbred. Selected inbred traits include: yield potential in hybrid combination; dry down; maturity; grain moisture at harvest; greensnap; resistance to root lodging; resistance to stalk lodging; grain quality; disease and insect resistance; ear and plant height; performance in different soil types, such as low organic matter content, clay, sand, black, high pH, low pH; and performance in wet environments, drought environments, and no tillage conditions. These inbred traits are thought to be governed by a complex genetic system that makes selection and breeding of a desired inbred line challenging. Even if an inbred line in hybrid combination exhibits excellent yield (a desired characteristic), this hybrid combination may still be less useful if the inbred lacks other parental traits such as deed yield, seed size, pollen production, good silks, plant height, and the like.

One challenging task associated with the development of an inbred line is the identification of individual plants that are genetically superior, because for many traits the true genotypic value is typically masked by other confounding plant traits or environmental factors. One method of identifying a superior individual plant is to observe its performance relative to other experimental plants and relative to widely grown standard cultivars. If a single observation is inconclusive, replicated observations provide a better estimate of a candidate inbred line's genetic worth.

Over time, methods of inbred line development and hybrid testing have been refined as a means to enhance hybrid performance in commercial maize production. Inbred development is typically accomplished using pedigree selection methods. Pedigree selection, as used herein, refers to selection within an F2 population produced from a planned cross of two breeder-selected genotypes, including elite inbred lines, progeny of synthetic varieties, open pollinated, composite, or backcross populations. Pedigree selection is known to be effective for highly heritable traits, but for less heritable traits such as yield, replicated test crosses at a variety of stages may ensure accurate selection.

Pedigree breeding starts with the crossing of two genotypes, each of which may have one or more desired characteristics that may be either lacking in the other genotype or that may complement the other genotype. If the original parental genotypes do not provide all of the desired characteristics, other genetic sources can be included in the breeding population. In the pedigree method, superior plants are selfed and selected in successive generations. Over each successive generation, the heterozygous genotypic condition gives way to homogeneous lines as a result of repeated generations of self-pollination and selection. Typically, at least five or more generations of selfing and selection are performed in the pedigree breeding method: F1→F2; F2→F3; F3→F4; F4→F5, and so on.

Backcrossing may also be used to improve an inbred line. Backcrossing transfers a specific desirable trait from one inbred or source to an inbred that lacks that trait. For example, backcrossing may be accomplished by first crossing a superior inbred (recurrent parent) to a donor inbred (non-recurrent parent) that carries the appropriate gene(s) for the trait in question. The progeny of this cross is then mated back to the superior inbred (recurrent parent) followed by selection within the resultant progeny for the desired trait transferred from the non-recurrent parent. After five or more backcross generations with selection for this desired trait, the resulting progeny are heterozygous for loci controlling the transferred characteristic, yet still resemble the superior parent for almost all other genes. The final backcross generation is typically selfed to produce pure breeding progeny for the characteristic being transferred.

Once the inbreds associated with the best hybrid performance have been identified using one or more of the methods described above, the hybrid seed can be reproduced indefinitely as long as the homogeneity of the inbred parent is maintained. A single-cross hybrid is produced by crossing two inbred lines to produce the first generation (F1) progeny. A double-cross hybrid is produced by crossing four inbred lines in pairs (A×B and C×D) followed by a crossing of the resulting F1 hybrids (A×B)×(C×D). Typically, much of the hybrid vigor exhibited by F1 hybrids is lost in the next generation (F2). Consequently, seeds harvested from hybrid variety crops are not typically used for planting stock.

Hybrid corn seed is typically produced by a male sterility system incorporating manual or mechanical detasseling. Alternate strips of two corn inbreds are planted in a field, and the pollen-bearing tassels are removed from one of the inbreds (female). Providing that there is sufficient isolation from sources of foreign corn pollen, the ears of the detasseled inbred will be fertilized only from the other inbred (male), and the resulting seed is therefore hybrid and will form hybrid plants.

The laborious, and occasionally unreliable, detasseling process can be avoided by using cytoplasmic male-sterile (CMS) inbreds. Plants of a CMS inbred are male sterile as a result of factors resulting from the cytoplasmic, as opposed to the nuclear, genome. Thus, this characteristic is inherited exclusively through the female parent in corn plants, since only the female provides cytoplasm to the fertilized seed. CMS plants are fertilized with pollen from another inbred that is not male-sterile. Pollen from the second inbred may or may not contribute genes that make the hybrid plants male-fertile. Seed from detasseled fertile corn and CMS-produced seed of the same hybrid can be blended to insure that adequate pollen loads are available for fertilization when the hybrid plants are grown.

There are several methods of conferring genetic male sterility available, such as multiple mutant genes at separate locations within the genome that confer male sterility, as disclosed in U.S. Pat. Nos. 4,654,465 and 4,727,219 and chromosomal translocations as described in U.S. Pat. Nos. 3,861,709 and 3,710,511, wherein the content of each is incorporated by reference in its entirety. In addition to these methods, U.S. Pat. No. 5,432,068, the contents of which are incorporated by reference in its entirety, describes a system of nuclear male sterility which includes: identifying a gene which is critical to male fertility, silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

Additional methods of conferring genetic male sterility are known in the art, each with associated benefits and drawbacks. These additional methods use a variety of approaches, such as delivering into the plant a gene encoding a cytotoxic substance associated with a male tissue specific promoter or an anti-sense system in which a gene critical to fertility is identified and an antisense to that gene is inserted in the plant, as described in PCT Published Application No. WO90/08828, the content of which is incorporated by reference in its entirety.

Another method of imparting male sterility makes use of gametocides administered to the plants using a topical application of chemicals. These chemicals affect cells that are critical to male fertility, and impact fertility in the plants only for the growing season in which the gametocide is applied, as described in U.S. Pat. No. 4,936,904, the content of which is incorporated by reference in its entirety. Application of the gametocide, timing of the application and genotype specificity of the gametocide may influence the usefulness of this approach.

SUMMARY

In one aspect, seed of corn inbred line designated MDS2713, representative seed of the line having been deposited under ATCC Accession No. PTA-127082, is provided. Applicant has made a deposit of tissue of seed of corn inbred line designated MDS2713 with the American Type Culture Collection (ATCC), 10801 University Boulevard, Manassas, Va. 20110 USA, as ATCC Accession No. PTA-127082. The deposit was made and accepted under the Budapest Treaty. Access to this deposit will be available during the pendency of the application to the Commissioner of Patents and Trademarks and persons determined by the Commissioner to be entitled thereto upon request. Upon issuance of any claims in the application, the deposited tissue will be irrevocably and without restriction released to the public upon the issuance of a patent, and will be publicly available for the enforceable life of the patent, and that evidence of a test of the viability of the biological material will be provided at the time of deposit. This deposit of corn inbred line designated MDS2713 will be maintained in the ATCC depository, which is a public depository, for a period of 30 years, or 5 years after the most recent request, or for the enforceable life of the patent, whichever is longer, and will be replaced if it becomes nonviable during that period. Additionally, Applicant has or will satisfy all the requirements of 37 C.F.R. §§ 1.801-1.809, including providing an indication of the viability of the sample upon deposit.

In another aspect, a method of producing a hybrid corn seed is provided. The method includes: (a) planting, in pollinating proximity, seeds of corn inbred lines MDS2713 and another inbred line; (b) inducing a lack of pollen production by plants of one of the corn inbred lines; (c) allowing natural cross-pollinating to occur between the plants of the corn inbred lines; and (d) harvesting the hybrid corn seed produced on cross-pollinated plants of the corn inbred lines.

DETAILED DESCRIPTION

Inbred corn line MDS2713 is a dent corn with superior characteristics resulting in increased yield and corn agronomics. MDS2713 further provides an excellent parental line for production of first generation (F1) hybrid corn. MDS2713 has a distinct kernel color and texture as compared to other "yellow dent" inbred corn varieties.

Yield and other data, provided below, demonstrate the effectiveness of the disclosed MDS2713 inbred corn line. At the time of MDS2713 development, the yield data showed an increase of around 5-10 bushels/acre over similar inbred lines within that maturity range. MDS2713 has also been shown to be effective at providing good grain quality and durability in tough conditions, and a high test weight, indicating suitability for utilization of MDS2713 hybrids in the production of food-grade products.

$$\text{Heat Units} = \frac{[\text{Max. Temp. } (\leq 86° \text{ F.}) + \text{Min. Temp. } (\geq 50° \text{ F.})]}{2} - 50$$

MDS2713 can be used in hybrid development for hybrids ranging between 106-118RM, corresponding to roughly Northern Illinois to Mexico and Colorado to the Eastern Seaboard. The agronomics and health of MDS2713 have been shown to be beneficial for the farmer looking for a hybrid with good grain quality and durability in tough conditions.

Standard pedigree ear-row selection method was used to develop the MDS2713 inbred line using two existing seed lines: 2369 and PHG39. Detasselled 2369 corn plants were crossed with PHG39 plants, and detasselled F1 plants were again crossed with PHG39 plants, and the resulting F2 seeds from the F1 plants were grown and subjected to selfing and selection for at least eight generations in the development of MDS2713. In this aspect, the background of the disclosed MDS2713 inbred line is (2369/PHG39*2). The selection criteria used during the development of MDS2713 were: grain yield; high plant density tolerance, good stand establishment, silking and pollen shedding ability, stalk and root strength, stay green appearance during senescence, seed quality and disease tolerance.

A comparison between characteristics of MDS2713 and the parent inbred lines, 2369 and PHG39, is shown in Table 1 below.

TABLE 1

Traits of MDS2713, 2369, and PHG39

| | MDS2713 | 2369 | PHG39 |
|---|---|---|---|
| Best adapted for: | Unavailable | Most regions | Most regions |
| Type: | Yellow Dent | Yellow Dent | Yellow Dent |
| Days from Emergence to 50% of plants in silk: | Unavailable | 68 | 79 |
| Heat unit silk: | 1698 | 1397 | 1575 |

$$\text{Heat Units} = \frac{[\text{Max. Temp.}(\leq 86°\text{ F.}) + \text{Min. Temp.}(\geq 50°\text{ F.})]}{2} - 50$$

Plant

| | MDS2713 | 2369 | PHG39 |
|---|---|---|---|
| Plant height (to tassel tip): | 198 cm | 212 cm | 253 cm |
| Ear height (to base of top ear): | 21.5 cm | 76 cm | 96 cm |
| Length of top ear internode: | 13 cm | 10 cm | 6 cm |
| Number of ears per stalk: | Two-ear tendency | Single | Single |
| Number of tillers: | None | None | None |

Leaf

| | MDS2713 | 2369 | PHG39 |
|---|---|---|---|
| Leaf Color: | Green-Yellow (7.5GY 3/4) | Dark Green (B14) | Dark Green (B14) |
| Angle from stalk: | 10°-49° | <30° | <30° |
| Marginal waves: | 2.56[a] | None (HY) | None (HY) |
| Number of leaves (mature plants): | 5 | 17 | 19 |
| Sheath Pubescence: | 1.08[a] | Light (W22) | Light (W22) |
| Longitudinal Creases: | 2[a] | Few (OH56A) | Few (OH56A) |
| Length (ear node leaf): | 78 cm | 74 cm | 91 cm |
| Width (widest point of ear node leaf): | 4 cm | 9 cm | 10 cm |

Tassel

| | MDS2713 | 2369 | PHG39 |
|---|---|---|---|
| Number of lateral branches: | 2.5 | 7 | 8 |
| Branch angle from central spike: | 2°-57° | <30° | >45° |
| Penduncle length (top leaf to basal branch): | 48 cm | N/A | 25 cm |
| Pollen shed: | 3.48[b] | Medium | Heavy (KY21) |
| Anther color: | Yellow | Pink | Greenish yellow, secondary |
| Glume color: | Green-Yellow | Green with red strip | Pale yellow green, secondary |

Ear

| | MDS2713 | 2369 | PHG39 |
|---|---|---|---|
| Length: | 18 cm | 18 cm | 18 cm |
| Weight: | 145 gm | 130 gm | 78 gm |
| Mid-point diameter: | 34 mm | 42 mm | 34 mm |
| Silk color: | Green-Yellow | Pink | Green |
| Fresh husk color: | Green-Yellow | Dark green | Dark green |
| Dry husk color: | Yellow | Buff | Pale brownish pink |
| Shank length: | 12 cm | 10 cm | 13 cm |
| Shank (no. of internodes): | Unavailable | 5 | 6 |
| Taper of ear: | 2[c] | Slight | Slight |
| Number of kernel rows: | 14 | 16 | 12 |
| Husk leaf: | Unavailable | Short (<8 cm) | Long (>15 cm) |
| Husk extension: | Medium (<8 cm) | Medium (barely covering ear) | Long (8-10 cm beyond ear tip) |
| Position at dry husk phase: | Upright | Upright | Upright |

TABLE 1-continued

Traits of MDS2713, 2369, and PHG39

| | MDS2713 | 2369 | PHG39 |
|---|---|---|---|

Dried Kernel

| | MDS2713 | 2369 | PHG39 |
|---|---|---|---|
| Size (from ear midpoint) | | | |
| Length: | 9.5 mm | 10 mm | 9 mm |
| Width: | 7.5 mm | 7 mm | 8 mm |
| Thickness: | 6 mm | 4 mm | 7 mm |
| Shape grade (% rounds): | 42 | 20-40 | 20-40 |
| Pericarp color: | Unavailable | Colorless | Translucent white |
| Aleurone color: | Yellow | Homozygous, White | Homozygous, opaque white |
| Endosperm color: | Yellow-red | Yellow | Deep orange yellow |
| Endosperm type: | Normal starch | Normal starch | Normal starch |
| Weight per 100 seeds: | 30 g | 26 g | 29 g |

Cob

| | MDS2713 | 2369 | PHG39 |
|---|---|---|---|
| Diameter at midpoint: | 18.5 mm | 25 mm | 22 mm |
| Strength: | Unavailable | Strong | Strong |
| Color: | Yellow | Red | White |

Disease Resistance

| | MDS2713 | 2369 | PHG39 |
|---|---|---|---|
| Northern Leaf Blight: | Unavailable | Resistant | Susceptible |
| Southern Leaf Blight: | Unavailable | Resistant | Tolerant |
| Corn Smut (common) | Unavailable | Resistant | Tolerant |
| Stalk Rot (Diplodia) | Unavailable | Not tested | Tolerant |
| Southern Rust | Unavailable | Not tested | Susceptible |
| Stalk Rot (Fusarium) | Unavailable | Not tested | Tolerant |
| Maize Dwarf Mosaic | Unavailable | Not tested | Susceptible |
| Stalk Rot (Gibberella) | Unavailable | Not tested | Tolerant |
| Smut (Head Smut) | Unavailable | Not tested | Tolerant |
| Bacterial Wilt (Stewart's) | Unavailable | Not tested | Susceptible |

Insect Resistance

| | MDS2713 | 2369 | PHG39 |
|---|---|---|---|
| European Cornborer | Unavailable | Resistant | Susceptible |
| Earworm | Unavailable | Unavailable | Susceptible |
| Rootworm (Western) | Unavailable | Unavailable | Susceptible |
| Aphid | Unavailable | Unavailable | Susceptible |

[a] 1 (none)-9 (many)
[b] 0 (Male Sterile)-9 (Heavy Shed)
[c] 1 (Slight Taper), 2 (Average Taper), 3 (Extreme Taper)

The 2369 inbred line most closely resembles the B73 inbred line. The leaf color of the 2369 inbred line is darker green as compared to the B73 inbred line. The ear of the 2369 inbred line is 18 cm long and 74 cm wide at the midpoint, as compared to corresponding dimensions of 18 cm and 42 cm for the ear of the B73 inbred line. The ear of the 2369 inbred line has 16 kernel rows as compared to 18 kernel rows for the ear of the B73 inbred line. Further, the 2369 inbred line attained maximum pollen 12 heat units before the B73 inbred line, and attained mid-silk 62 heat units prior to the B73 inbred line. Yield for the 2369 inbred line is 18 bushels higher, 3.1 moisture points dryer, and had a 0.6 better stalk rating and 0.5 better root rating as compared to the B73 inbred line.

The PHG39 inbred line most closely resembles the B73 inbred line. The plant height of the PHG39 inbred line is 253 cm as compared to the 251 cm plant height of the B73 inbred line. The ear of the PHG39 inbred line is 14 cm lower-eared as compared to the B73 inbred line. The ear of the PHG39 inbred line has indistinct kernel rows as compared to the straight, distinct kernel rows of the B73 inbred line. The ear of the PHG39 inbred line is 18 cm long and 34 cm wide at the midpoint, as compared to corresponding dimensions of 15 cm and 42 cm for the ear of the B73 inbred line.

This disclosure is also directed to methods for producing a corn plant by crossing a first parent corn plant with a second parent corn plant, wherein the first or second corn plant is the inbred corn plant from the line MDS2713. Further, both first and second parent corn plants may be from the inbred line MDS2713. Therefore, any methods using the inbred corn line MDS2713 are part of this disclosure: selfing, backcrosses, hybrid breeding, and crosses to populations. Any plants produced using inbred corn line MDS2713 as parents are within the scope of this disclosure. Advantageously, the inbred corn line MDS2713 is used in crosses with other corn varieties to produce first generation (F1) corn hybrid seed and plants with superior characteristics.

Some of the criteria used to select ears in various generations include: yield, stalk quality, root quality, disease tolerance, late plant greenness, late season plant intactness, ear retention, pollen shedding ability and silking ability. During the development of the line, crosses were made to inbred testers for the purpose of estimating the line's general and specific combining ability. The inbred was evaluated further as a line and in numerous crosses by other research stations. The inbred has proven to have a very good combining ability in hybrid combinations.

The inbred has shown uniformity and stability within the limits of environmental influence for the traits. It has been self-pollinated and ear-rowed a sufficient number of generations, with careful attention to uniformity of plant type to ensure homozygosity and phenotypic stability necessary to use in commercial production. The line has been increased both by hand and sibbed in isolated fields with continued observations for uniformity. No variant traits have been observed or are expected in MDS2713.

This disclosure also is directed to methods for producing a corn plant by crossing a first parent corn plant with a second parent corn plant wherein either the first or second parent corn plant is an inbred corn plant of the line MDS2713. Further, both first and second parent corn plants can come from the inbred corn line MDS2713. Still further, this disclosure also is directed to methods for producing an inbred corn line MDS2713-derived corn plant by crossing inbred corn line MDS2713 with a second corn plant and growing the progeny seed, and repeating the crossing and growing steps with the inbred corn line MDS2713-derived plant from 0 to 7 times. Thus, any such methods using the inbred corn line MDS2713 are part of this disclosure: selfing, backcrosses, hybrid production, crosses to populations, and the like. All plants produced using inbred corn line MDS2713 as a parent are within the scope of this disclosure, including plants derived from inbred corn line MDS2713. Advantageously, the inbred corn line is used in crosses with other, different, corn inbreds to produce first generation (F1) corn hybrid seeds and plants with superior characteristics.

It should be understood that the inbred can, through routine manipulation of cytoplasmic or other factors, be produced in a male-sterile form. Such embodiments are also contemplated within the scope of the present claims.

As used herein, the term plant includes plant cells, plant protoplasts, plant cell tissue cultures from which corn plants can be regenerated, plant calli, plant clumps and plant cells that are intact in plants or parts of plants, such as embryos, pollen, ovules, flowers, kernels, ears, cobs, leaves, husks, stalks, roots, root tips, anthers, silk and the like. The generation of plant calli from plant parts, and the regeneration of plants from plant calli may make use of any method known in the art, including, but not limited to, the methods as described in Duncan, et al., Planta 165:322-332 (1985), Songstad, et al., Plant Cell Reports 7:262-265 (1988), K. P. Rao et al., Maize Genetics Cooperation Newsletter, 60:64-65 (1986), and B. V. Conger, et al., Plant Cell Reports, 6:345-347 (1987), wherein the disclosure of each is incorporated by reference herein in its entirety.

In an aspect, tissue culture may be used to provide cells which upon growth and differentiation produce corn plants having the physiological and morphological characteristics of inbred corn line MDS2713. Tissue culture of corn may make use of any method known in the art, including, but not limited to, the methods as described in is described in European Patent Publication No. EP160390, Green and Rhodes, "Plant Regeneration in Tissue Culture of Maize," Maize for Biological Research (Plant Molecular Biology Association, Charlottesville, Va. 367-372, (1982)) and in Duncan et al., "The Production of Callus Capable of Plant Regeneration from Immature Embryos of Numerous *Zea mays* Genotypes," 165 Planta 322:332 (1985), wherein the disclosure of each is incorporated by reference herein in its entirety.

Corn is used as human food, livestock feed, and as raw material in industry. The food uses of corn, in addition to human consumption of corn kernels, include both products of dry- and wet-milling industries. The principal products of corn dry milling are grits, meal and flour. The corn wet-milling industry can provide corn starch, corn syrups, and dextrose for food use. Corn oil is recovered from corn germ, which is a by-product of both dry- and wet-milling industries.

Other industrial uses of corn include production of ethanol, corn starch in the wet-milling industry and corn flour in the dry-milling industry. The industrial applications of corn starch and flour are based on functional properties, such as viscosity, film formation, adhesive properties, and ability to suspend particles. The corn starch and flour have application in the paper and textile industries. Other industrial uses include applications in adhesives, building materials, foundry binders, laundry starches, explosives, oil-well muds and other mining applications.

Plant parts other than the grain of corn are also used in industry, for example: stalks and husks are made into paper and wallboard and cobs are used for fuel and to make charcoal.

In the tables that follow, the traits and characteristics of inbred corn line MDS2713 are given in hybrid combination. The data collected on inbred corn line MDS2713 is presented for the key characteristics and traits. The tables present yield test information about MDS2713. MDS2713 was tested in several hybrid combinations at numerous locations, with several replications per location. Information about these hybrids, as compared to several check hybrids, is presented.

TABLE 2

Traits and characteristics of MDS2713*MBS8731 hybrids.

|  | Yield | % M | % STD | % SL | % RL | TW | $/A |
|---|---|---|---|---|---|---|---|
| MDS2713*MBS8731 | 187.94 | 18.26 | 96.41 | 0.92 | 5.15 | 56.47 | $ 715.45 |
| DKC66-96 | 204.59 | 17.68 | 96.19 | 1.47 | 5.10 | 58.19 | $ 787.13 |
| Reps 40 \| Years 1 \| States 11 | −16.6 | +0.6 | +0.2 | −0.5 | +0.1 | −1.7 | −$ 71.68 |
| MDS2713*MBS8731 | 208.89 | 19.38 | 95.15 | 0.98 | 2.87 | 56.33 | $ 778.85 |
| DKC67-72VT2P | 229.51 | 18.77 | 96.59 | 3.34 | 1.63 | 56.80 | $ 865.56 |
| Reps 76 \| Years 2 \| States 14 | −20.6 | +0.6 | −1.4 | −2.4 | +1.2 | −0.5 | −$ 86.71 |
| MDS2713*MBS8731 | 202.63 | 18.67 | 96.79 | 0.60 | 3.83 | 56.41 | $ 765.53 |
| GP280*MBS8814GTCBLLRW | 214.17 | 19.81 | 94.86 | 0.58 | 3.97 | 57.39 | $ 792.12 |
| Reps 61 \| Years 2 \| States 11 | −11.5 | −1.1 | +1.9 | +0.0 | −0.1 | −1.0 | −$ 26.59 |
| MDS2713*MBS8731 | 201.45 | 19.25 | 94.17 | 1.36 | 3.39 | 56.33 | $ 752.86 |
| GP280GTCBLLBL*MBS8814 | 214.19 | 20.00 | 96.85 | 0.69 | 5.83 | 57.24 | $ 789.24 |
| Reps 54 \| Years 1 \| States 13 | −12.7 | −0.7 | −2.7 | +0.7 | −2.4 | −0.9 | −$ 36.38 |
| MDS2713*MBS8731 | 201.66 | 18.99 | 95.58 | 0.96 | 3.62 | 56.38 | $ 757.36 |
| GP286*MBS8814GTCBLLRW | 204.59 | 20.73 | 92.89 | 1.23 | 5.66 | 56.73 | $ 743.42 |
| Reps 116 \| Years 3 \| States 14 | −2.9 | −1.7 | +2.7 | −0.3 | −2.0 | −0.4 | +$ 13.94 |
| MDS2713*MBS8731 | 174.29 | 18.37 | 97.83 | 1.81 | 4.79 | 55.75 | $ 662.19 |
| GP570GTCBLL*MBS8731 | 192.37 | 16.56 | 97.42 | 0.00 | 7.70 | 54.93 | $ 755.25 |
| Reps 19 \| Years 1 \| States 8 | −18.1 | +1.8 | +0.4 | +1.8 | −2.9 | +0.8 | −$ 93.05 |
| MDS2713*MBS8731 | 187.94 | 18.26 | 96.41 | 0.92 | 5.15 | 56.47 | $ 715.45 |
| GP632*GP633GTCBLLRW | 203.67 | 18.45 | 97.73 | 0.88 | 3.64 | 56.61 | $ 772.64 |
| Reps 40 \| Years 1 \| States 11 | −15.7 | −0.2 | −1.3 | +0.0 | +1.5 | −0.1 | −$ 57.19 |
| MDS2713*MBS8731 | 227.15 | 19.68 | 97.54 | 0.06 | 1.62 | 56.33 | $ 842.08 |
| GP632GTCBLL*GP633HX4 | 204.01 | 19.83 | 98.21 | 0.27 | 0.44 | 57.08 | $ 754.13 |
| Reps 22 \| Years 1 \| States 9 | +23.1 | −0.2 | −0.7 | −0.2 | +1.2 | −0.7 | +$ 87.95 |
| MDS2713*MBS8731 | 208.89 | 19.38 | 95.15 | 0.98 | 2.87 | 56.33 | $ 778.85 |
| PIONEER HYBRID 1637AM | 237.46 | 18.73 | 96.78 | 1.02 | 1.11 | 58.38 | $ 896.17 |
| Reps 76 \| Years 2 \| States 14 | −28.6 | +0.7 | −1.6 | −0.0 | +1.8 | −2.0 | −$ 117.33 |
| MDS2713*MBS8731 | 203.64 | 18.87 | 96.80 | 0.61 | 3.90 | 56.44 | $ 766.52 |
| PIONEER HYBRID 2088AM | 219.60 | 18.99 | 97.45 | 0.64 | 7.46 | 56.96 | $ 824.70 |
| Reps 61 \| Years 2 \| States 11 | −16.0 | −0.1 | −0.7 | −0.0 | −3.6 | −0.5 | −$ 58.18 |

TABLE 3

Traits and characteristics of MDS2713*MBS8814GTCBLLRW hybrids.

|  | Yield | % M | % STD | % SL | % RL | TW | $/A |
|---|---|---|---|---|---|---|---|
| MDS2713*MBS8814GTCBLLRW | 201.93 | 20.02 | 96.00 | 0.46 | 5.33 | 56.86 | $ 743.89 |
| DKC66-96 | 208.68 | 17.93 | 97.59 | 1.06 | 6.58 | 58.67 | $ 799.24 |
| Reps 59 \| Years 2 \| States 12 | −6.8 | +2.1 | −1.6 | −0.6 | −1.2 | −1.8 | −$ 55.36 |
| MDS2713*MBS8814GTCBLLRW | 219.26 | 20.29 | 96.00 | 0.28 | 2.89 | 56.77 | $ 803.55 |
| DKC67-72VT2P | 229.88 | 18.85 | 96.68 | 3.25 | 1.58 | 56.80 | $ 865.65 |
| Reps 78 \| Years 2 \| States 14 | −10.6 | +1.4 | −0.7 | −3.0 | +1.3 | −0.0 | −$ 62.10 |
| MDS2713*MBS8814GTCBLLRW | 210.75 | 20.23 | 96.92 | 0.89 | 4.23 | 56.79 | $ 773.26 |
| GP280*MBS8814GTCBLLRW | 215.32 | 20.03 | 95.86 | 0.82 | 5.21 | 57.45 | $ 792.96 |
| Reps 92 \| Years 4 \| States 12 | −4.6 | +0.2 | +1.1 | +0.1 | −1.0 | −0.7 | −$ 19.69 |
| MDS2713*MBS8814GTCBLLRW | 211.80 | 20.17 | 96.00 | 0.36 | 3.91 | 56.81 | $ 777.94 |
| GP286*MBS8814GTCBLLRW | 207.71 | 20.78 | 94.10 | 1.14 | 6.33 | 56.89 | $ 754.14 |
| Reps 137 \| Years 4 \| States 15 | +4.1 | −0.6 | +1.9 | −0.8 | −2.4 | −0.1 | +$ 23.80 |
| MDS2713*MBS8814GTCBLLRW | 199.28 | 20.49 | 92.33 | 0.53 | 6.29 | 56.11 | $ 727.55 |
| GP570GTCBLL*MBS8731 | 199.60 | 16.99 | 97.28 | 0.00 | 8.21 | 55.20 | $ 777.59 |
| Reps 18 \| Years 1 \| States 8 | −0.3 | +3.5 | −4.9 | +0.5 | −1.9 | +0.9 | −$ 50.04 |
| MDS2713*MBS8814GTCBLLRW | 200.96 | 20.17 | 94.83 | 1.46 | 5.04 | 56.46 | $ 738.21 |
| GP632*GP633GTCBLLRW | 206.77 | 18.86 | 97.96 | 0.97 | 2.93 | 56.69 | $ 778.47 |

TABLE 3-continued

Traits and characteristics of MDS2713*MBS8814GTCBLLRW hybrids.

| | Yield | % M | % STD | % SL | % RL | TW | $/A |
|---|---|---|---|---|---|---|---|
| Reps 49 | Years 2 | States 11 | −5.8 | +1.3 | −3.1 | +0.5 | +2.1 | −0.2 | −$ 40.26 |
| MDS2713*MBS8814GTCBLLRW | 235.10 | 21.18 | 98.81 | 0.16 | 2.43 | 56.90 | $ 846.87 |
| GP632GTCBLL*GP633HX4 | 201.34 | 19.87 | 98.36 | 0.24 | 0.40 | 57.08 | $ 743.83 |
| Reps 24 | Years 1 | States 9 | +33.8 | +1.3 | +0.4 | −0.1 | +2.0 | −0.2 | +$ 103.04 |
| MDS2713*MBS8814GTCBLLRW | 203.96 | 20.45 | 96.52 | 1.56 | 4.76 | 56.64 | $ 745.12 |
| MBS3520*MBS8814GTCBLLRW | 197.65 | 17.92 | 97.36 | 1.10 | 6.81 | 55.84 | $ 757.04 |
| Reps 47 | Years 3 | States 10 | +6.3 | +2.5 | −0.8 | +0.5 | −2.1 | +0.8 | −$ 11.93 |
| MDS2713*MBS8814GTCBLLRW | 204.15 | 19.94 | 99.18 | 0.50 | 4.54 | 57.49 | $ 753.19 |
| MBS3773*MBS8814GTCBLLRW | 200.13 | 18.86 | 98.14 | 0.83 | 4.66 | 57.30 | $ 753.45 |
| Reps 20 | Years 1 | States 9 | +4.0 | +1.1 | +1.0 | −0.3 | −0.1 | +0.2 | −$ 0.27 |
| MDS2713*MBS8814GTCBLLRW | 204.15 | 19.94 | 99.18 | 0.50 | 4.54 | 57.49 | $ 753.19 |
| PIONEER HYBRID 1498HR | 201.32 | 17.51 | 99.27 | 0.00 | 3.58 | 59.00 | $ 777.03 |
| Reps 20 | Years 1 | States 9 | +2.8 | +2.4 | −0.1 | +0.5 | +1.0 | −1.5 | −$ 23.84 |
| MDS2713*MBS8814GTCBLLRW | 219.26 | 20.29 | 96.00 | 0.28 | 2.89 | 56.77 | $ 803.55 |
| PIONEER HYBRID 1637AM | 236.66 | 18.78 | 96.87 | 1.00 | 1.08 | 58.38 | $ 892.24 |
| Reps 78 | Years 2 | States 14 | −17.4 | +1.5 | −0.9 | −0.7 | +1.8 | −1.6 | −$ 88.70 |
| MDS2713*MBS8814GTCBLLRW | 212.88 | 20.45 | 97.07 | 0.38 | 4.52 | 56.89 | $ 777.70 |
| PIONEER HYBRID 2088AM | 219.17 | 18.95 | 97.86 | 0.55 | 6.70 | 57.20 | $ 823.75 |
| Reps 82 | Years 3 | States 12 | −6.3 | +1.5 | −0.8 | −0.2 | −2.2 | −0.3 | −$ 46.04 |

TABLE 4

Traits and characteristics of MDS2713*GP633GTCBLLRW hybrids.

| | Yield | % M | % STD | % SL | % RL | TW | $/A |
|---|---|---|---|---|---|---|---|
| MDS2713*GP633GTCBLLRW | 220.43 | 20.09 | 99.79 | 6.64 | 11.43 | 56.52 | $ 810.94 |
| DKC62-97RIB | 219.75 | 17.91 | 99.79 | 2.69 | 1.62 | 56.91 | $ 841.91 |
| Reps 28 | Years 1 | States 5 | +0.7 | +2.2 | +0.0 | +3.9 | +9.8 | −0.4 | −$ 30.97 |
| MDS2713*GP633GTCBLLRW | 180.38 | 18.87 | 93.77 | 3.02 | 12.07 | 57.78 | $ 679.03 |
| DKC66-96 | 183.47 | 18.21 | 94.36 | 3.30 | 7.68 | 57.40 | $ 699.04 |
| Reps 19 | Years 1 | States 8 | −3.1 | +0.7 | −0.6 | −0.3 | +4.4 | +0.4 | −$ 20.01 |
| MDS2713*GP633GTCBLLRW | 180.60 | 18.57 | 93.71 | 3.02 | 12.07 | 57.65 | $ 683.54 |
| GP280*MBS8814GTCBLLRW | 199.56 | 19.48 | 94.24 | 0.62 | 6.28 | 56.05 | $ 742.65 |
| Reps 18 | Years 1 | States 8 | −19.0 | −0.9 | −0.5 | +2.4 | +5.8 | +1.6 | −$ 59.11 |
| MDS2713*GP633GTCBLLRW | 180.38 | 18.87 | 93.77 | 3.02 | 12.07 | 57.78 | $ 679.03 |
| GP286*MBS8814GTCBLLRW | 191.84 | 20.74 | 89.52 | 0.00 | 6.08 | 56.09 | $ 696.94 |
| Reps 19 | Years 1 | States 8 | −11.5 | −1.9 | +4.3 | +3.0 | +6.0 | +1.7 | −$ 17.91 |
| MDS2713*GP633GTCBLLRW | 180.38 | 18.87 | 93.77 | 3.02 | 12.07 | 57.78 | $ 679.03 |
| GP570GTCBLL*MBS8731 | 192.37 | 16.56 | 97.42 | 0.00 | 7.70 | 54.93 | $ 755.25 |
| Reps 19 | Years 1 | States 8 | −12.0 | +2.3 | −3.6 | +3.0 | +4.4 | +2.8 | −$ 76.22 |
| MDS2713*GP633GTCBLLRW | 220.43 | 20.09 | 99.79 | 6.64 | 11.43 | 56.52 | $ 810.94 |
| GP570GTCBLL*MBS8731HX1 | 238.97 | 18.81 | 99.58 | 4.66 | 7.74 | 54.93 | $ 900.60 |
| Reps 28 | Years 1 | States 5 | −18.5 | +1.3 | +0.2 | +2.0 | +3.7 | +1.6 | −$ 89.66 |
| MDS2713*GP633GTCBLLRW | 180.38 | 18.87 | 93.77 | 3.02 | 12.07 | 57.78 | $ 679.03 |
| GP632*GP633GTCBLLRW | 194.68 | 18.71 | 97.90 | 1.89 | 1.05 | 55.98 | $ 734.99 |
| Reps 19 | Years 1 | States 8 | −14.3 | +0.2 | −4.1 | +1.1 | +11.0 | +1.8 | −$ 55.97 |
| MDS2713*GP633GTCBLLRW | 220.43 | 20.09 | 99.79 | 6.64 | 11.43 | 56.52 | $ 810.94 |
| GP709GTCBLLBL*GP633HX1 | 222.00 | 17.41 | 99.76 | 2.32 | 2.68 | 56.94 | $ 858.28 |
| Reps 28 | Years 1 | States 5 | −1.6 | +2.7 | +0.0 | +4.3 | +8.8 | −0.4 | −$ 47.34 |
| MDS2713*GP633GTCBLLRW | 220.43 | 20.09 | 99.79 | 6.64 | 11.43 | 56.52 | $ 810.94 |
| PIONEER HYBRID 1197AMXT | 233.79 | 17.73 | 99.68 | 2.57 | 1.23 | 56.24 | $ 898.67 |

TABLE 4-continued

Traits and characteristics of MDS2713*GP633GTCBLLRW hybrids.

|  | Yield | % M | % STD | % SL | % RL | TW | $/A |
|---|---|---|---|---|---|---|---|
| Reps 28 | Years 1 | States 5 | −13.4 | +2.4 | +0.1 | +4.1 | +10.2 | +0.3 | −$ 87.73 |
| MDS2713*GP633GTCBLLRW | 184.55 | 19.19 | 94.64 | 3.24 | 12.88 | 57.83 | $ 690.58 |
| PIONEER HYBRID 2088AM | 207.28 | 19.40 | 96.95 | 0.60 | 10.23 | 56.25 | $ 772.57 |
| Reps 18 | Years 1 | States 8 | −22.7 | −0.2 | −2.3 | +2.6 | +2.7 | +1.6 | −$ 81.99 |

TABLE 5

Traits and characteristics of MDS2713*MBS5411 hybrids.

|  | Yield | % M | % STD | % SL | % RL | TW | $/A |
|---|---|---|---|---|---|---|---|
| MDS2713*MBS5411 | 230.59 | 20.40 | 92.70 | 1.59 | 0.39 | 56.88 | $ 843.24 |
| DKC57-75RIB | 214.20 | 20.31 | 95.30 | 2.86 | 0.39 | 56.27 | $ 784.74 |
| Reps 12 | Years 1 | States 4 | +16.4 | +0.1 | −2.6 | −1.3 | +0.0 | +0.6 | +$ 58.50 |
| MDS2713*MBS5411 | 230.59 | 20.40 | 92.70 | 1.59 | 0.39 | 56.88 | $ 843.24 |
| MBS3644GTCBLLRW*MBS5411 | 224.64 | 19.58 | 97.01 | 0.55 | 0.25 | 56.39 | $ 834.32 |
| Reps 12 | Years 1 | States 4 | +6.0 | +0.8 | −4.3 | +1.0 | +0.1 | +0.5 | +$ 8.92 |
| MDS2713*MBS5411 | 230.59 | 20.40 | 92.70 | 1.59 | 0.39 | 56.88 | $ 843.24 |
| PIONEER HYBRID 0506AM | 218.65 | 19.38 | 94.45 | 0.26 | 1.14 | 57.09 | $ 815.18 |
| Reps 12 | Years 1 | States 4 | +11.9 | +1.0 | −1.8 | +1.3 | −0.7 | −0.2 | +$ 28.06 |
| MDS2713*MBS5411 | 226.40 | 19.87 | 91.23 | 1.91 | 0.47 | 57.58 | $ 836.33 |
| PIONEER HYBRID 0825AMXT | 248.65 | 19.38 | 94.87 | 1.22 | 2.73 | 54.65 | $ 927.08 |
| Reps 10 | Years 1 | States 3 | −22.3 | +0.5 | −3.6 | +0.7 | −2.3 | +2.9 | −$ 90.74 |
| MDS2713*MBS5411 | 230.59 | 20.40 | 92.70 | 1.59 | 0.39 | 56.88 | $ 843.24 |
| SGI094GTCBLLRWBL*GP614 | 231.53 | 20.30 | 95.73 | 0.98 | 0.89 | 55.29 | $ 848.29 |
| Reps 12 | Years 1 | States 4 | −0.9 | +0.1 | −3.0 | +0.6 | −0.5 | +1.6 | −$ 5.06 |

The headers of Tables 2-5 are defined as follows. Yield is the bushels of corn grown per acre in bushels per acre. % M is the moisture content in percent. % STD is the percent stand in percent. % SL is the stalk lodge in percent. % RL is the root lodge in percent. TW is the test weight in pounds per bushel. $/A is the cost to grow per acre in dollars per acre.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present disclosure, in particular embodiments, also relates to transformed versions of the claimed inbred line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed corn plants, using transformation methods as described below to incorporate transgenes into the genetic material of the corn plant(s).

In one aspect, the expression vectors used for plant transformation may include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. Positive selection methods are also known in the art.

One commonly used selectable marker gene for plant transformation is the neomycin phosphotransferase II (nptII) gene, which when placed under the control of plant regulatory signals confers resistance to kanamycin, as described in Fraley et al., Proc. Natl. Acad. Sci. U.S.A., 80:4803 (1983), the content of which is incorporated by reference herein in its entirety. Another commonly used selectable marker gene is the hygromycin phosphotransferase gene which confers resistance to the antibiotic hygromycin, as described in Vanden Elzen et al., Plant Mol. Biol., 5:299 (1985), the content of which is incorporated by reference herein in its entirety.

Additional selectable marker genes of bacterial origin that confer resistance to antibiotics include gentamycin acetyl transferase, streptomycin phosphotransferase, aminoglycoside-3'-adenyl transferase, the bleomycin resistance determinant, as described in Hayford et al., Plant Physiol. 86:1216 (1988), Jones et al., Mol. Gen. Genet., 210:86 (1987), Svab et al., Plant Mol. Biol. 14:197 (1990) and Hille et al., Plant Mol. Biol. 7:171 (1986), wherein the content of each is incorporated by reference herein in its entirety. Other selectable marker genes may include marker genes that confer resistance to herbicides such as glyphosate, glufosinate or broxynil, as described in Comai et al., Nature 317:741-744 (1985), Gordon-Kamm et al., Plant Cell 2:603-618 (1990) and Stalker et al., Science 242:419-423 (1988), wherein the content of each is incorporated by reference herein in its entirety.

Other selectable marker genes that may be included in an expression vectors used for plant transformation may include, for example, mouse dihydrofolate reductase, plant 5-enolpyruvylshikimate-3-phosphate synthase and plant acetolactate synthase, as described in Eichholtz et al., Somatic Cell Mol. Genet. 13:67 (1987), Shah et al., Science 233:478 (1986), and Charest et al., Plant Cell Rep. 8:643 (1990), wherein the content of each is incorporated by reference herein in its entirety.

Other selectable marker genes that may be included in the expression vectors used for plant transformation include marker genes that require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS, β-galactosidase, luciferase and chloramphenicol, acetyltransferase, as described in Jefferson, R. A., Plant Mol. Biol. Rep. 5:387 (1987), Teeri et al., EMBO J. 8:343 (1989), Koncz et al., Proc. Natl. Acad. Sci U.S.A. 84:131 (1987), and DeBlock et al., EMBO J. 3:1681 (1984), wherein the content of each is incorporated by reference herein in its entirety. Another approach to the identification of relatively rare transformation events has been use of a gene that encodes a dominant constitutive regulator of the *Zea mays* anthocyanin pigmentation pathway, as described in Ludwig et al., Science 247:449 (1990), the content of which is incorporated by reference herein in its entirety.

In various aspects, the genes included in expression vectors are enabled by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

An inducible promoter is operably linked to a gene for expression in corn. Optionally, the inducible promoter is operably linked to a nucleotide sequence encoding a signal sequence which is operably linked to a gene for expression in corn. With an inducible promoter the rate of transcription increases in response to an inducing agent.

Any inducible promoter can be used in the instant disclosure including, but not limited to, the inducible promoters described in Ward et al., Plant Mol. Biol. 22:361-366 (1993), inducible promoters from the ACEI system which responds to copper as described in Meft et al., PNAS 90:4567-4571 (1993), the In2 gene from maize which responds to benzenesulfonamide herbicide safeners as described in Hershey et al., Mol. Gen Genetics 227:229-237 (1991) and Gatz et al., Mol. Gen. Genetics 243:32-38 (1994), the Tet repressor from Tn10, as described in Gatz et al., Mol. Gen. Genetics 227:229-237 (1991), and a promoter from a steroid hormone gene, the transcriptional activity of which is induced by a glucocorticosteroid hormone as described in Schena et al., Proc. Natl. Acad. Sci. U.S.A. 88:0421 (1991), wherein the content of each is incorporated by reference herein in its entirety. In one aspect, the inducible promoter may be a promoter that responds to an inducing agent to which plants do not normally respond.

In various aspects, the genes included in expression vectors may include constitutive promoter. The constitutive promoter may be operably linked to a gene for expression in corn or the constitutive promoter may be operably linked to a nucleotide sequence encoding a signal sequence which is operably linked to a gene for expression in corn.

Many different constitutive promoters can be utilized in the instant disclosure without limitation. Non-limiting examples of suitable constitutive promoters include promoters from plant viruses such as the 35S promoter from CaMV as described in Odell et al., Nature 313:810-812 (1985), promoters from genes as rice actin as described in McElroy et al., Plant Cell 2:163-171 (1990)), the gene ubiquitin as described in Christensen et al., Plant Mol. Biol. 12:619-632 (1989) and in Christensen et al., Plant Mol. Biol. 18:675-689 (1992)), the gene pEMU as described in Last et al., Theor. Appl. Genet. 81:581-588 (1991)), the gene MAS as described in Velten et al., EMBO J. 3:2723-2730 (1984), and the maize H3 histone as described in Lepetit et al., Mol. Gen. Genetics 231:276-285 (1992) and Atanassova et al., Plant Journal 2 (3): 291-300 (1992), wherein the content of each is incorporated by reference herein in its entirety. The ALS promoter, XbaI/NcoI fragment 5' to the *Brassica napus* ALS3 structural gene (or a nucleotide sequence similarity to the Xba1/NcoI fragment), represents a useful constitutive promoter, as described in PCT Published Application No. WO96/30530.

In various aspects, the genes included in expression vectors may include tissue-specific promoter. A tissue-specific promoter is operably linked to a gene for expression in corn. Optionally, the tissue-specific promoter is operably linked to a nucleotide sequence encoding a signal sequence which is operably linked to a gene for expression in corn. Plants transformed with a gene of interest operably linked to a tissue-specific promoter produce the protein product of the transgene exclusively, or preferentially, in a specific tissue.

Any tissue-specific or tissue-preferred promoter can be utilized in the instant disclosure without limitation including, but not limited to, a root-preferred promoter, such as that from the phaseolin gene as described in Murai et al., Science 23:476-482 (1983) and in Sengupta-Gopalan et al., Proc. Natl. Acad. Sci. U.S.A. 82:3320-3324 (1985)); a leaf-specific and light-induced promoter such as that from cab or rubisco as described in Simpson et al., EMBO J. 4(11):2723-2729 (1985) and Timko et al., Nature 318:579-582 (1985)); an anther-specific promoter such as that from LAT52 as described in Twell et al., Mol. Gen. Genetics 217:240-245 (1989)); a pollen-specific promoter such as that from Zm13 as described in Guerrero et al., Mol. Gen. Genetics 244:161-168 (1993)); and a microspore-preferred promoter such as that from apg as described in Twell et al., Sex. Plant Reprod. 6:217-224 (1993), wherein the content of each is incorporated by reference herein in its entirety.

In various other aspects, the genes included in expression vectors may include signal sequences for targeting proteins to subcellular compartments. In these aspects, the transport of protein produced by transgenes to a subcellular compartment such as the chloroplast, vacuole, peroxisome, glyoxysome, cell wall or mitochondroin or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized. The presence of a signal sequence in the expression vector directs a polypeptide to either an intracellular organelle or subcellular compartment or for secretion to the apoplast. Many signal sequences are known in the art including, but not limited to, Becker et al., Plant Mol. Biol. 20:49 (1992); Close, P. S., Master's Thesis, Iowa State University (1993); Knox, C., et al., "Structure and Organization of Two Divergent Alpha-Amylase Genes from Barley"; Plant Mol. Biol. 9:3-17 (1987); Lerner et al., Plant Physiol. 91:124-129 (1989); Fontes et al., Plant Cell 3:483-496 (1991); Matsuoka et al., Proc. Natl. Acad. Sci. 88:834 (1991); Gould et al., J. Cell. Biol. 108:1657 (1989); Creissen et al., Plant J. 2:129 (1991); Kalderon, et al., Cell 39:499-509 (1984); and Steifel, et al., Plant Cell 2:785-793 (1990), wherein the content of each is incorporated by reference herein in its entirety.

With transgenic plants according to the present disclosure, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, Anal. Biochem. 114:92-6 (1981), the content of which is incorporated by reference herein in its entirety.

In other aspects, agronomic genes can be expressed in transformed plants. More particularly, plants can be genetically engineered to express various phenotypes of agronomic interest. Exemplary genes implicated in this regard include, but are not limited to, those categorized below.

Plant defenses are often activated by specific interaction between the product of a disease resistance gene (R) in the plant and the product of a corresponding avirulence (Avr) gene in the pathogen. A plant inbred line can be transformed with cloned resistance gene to engineer plants that are resistant to specific pathogen strains, as described in Jones et al., Science 266:789 (1994); Martin et al., Science 262: 1432 (1993); and Mindrinos et al., Cell 78:1089 (1994), wherein the content of each is incorporated by reference herein in its entirety.

In an aspect, the agronomic gene may include a *Bacillus thuringiensis* protein, a derivative thereof or a synthetic polypeptide modeled thereon, as described in Geiser et al., Gene 48:109 (1986), the content of which is incorporated by reference herein in its entirety, and DNA molecules encoding δ-endotoxin genes purchased from American Type Culture Collection, Manassas, Va., for example, under ATCC Accession Nos. 40098, 67136, 31995 and 31998.

In an aspect, the agronomic gene may include a lectin such as nucleotide sequences of several *Clivia miniata* mannose-binding lectin genes, as described by Van Damme et al., Plant Molec. Biol. 24:25 (1994), the content of which is incorporated by reference herein in its entirety. In an aspect, the agronomic gene may include a vitamin-binding protein such as avidin as described in PCT Published Application No. WO93/06487, the content of which is hereby incorporated by reference in its entirety. In an aspect, the agronomic gene may include an enzyme inhibitor, for example, a protease or proteinase inhibitor or an amylase inhibitor as described in Abe et al., J. Biol. Chem. 262:16793 (1987), Huub et al., Plant Molec. Biol. 21:985 (1993), and Sumitani et al., Biosci. Biotech. Biochem. 57:1243 (1993), wherein the content of each is incorporated by reference herein in its entirety. In an aspect, the agronomic gene may include an insect-specific hormone or pheromone such as an ecdysteroid and juvenile hormone, a variant thereof, a mimetic based thereon, or an antagonist or agonist thereof, as described in Hammock et al., Nature 344:458 (1990), the content of which is incorporated by reference herein in its entirety. In an aspect, the agronomic gene may include an insect-specific peptide or neuropeptide which, upon expression, disrupts the physiology of the affected pest, as described in Regan, J. Biol. Chem. 269:9 (1994), Pratt et al., Biochem. Biophys. Res. Comm. 163:1243 (1989), and U.S. Pat. No. 5,266,317, wherein the content of each is incorporated by reference herein in its entirety. In an aspect, the agronomic gene may include an insect-specific venom produced in nature by a snake, a wasp, etc. as described, by way of non-limiting example, in Pang et al., Gene 116:165 (1992), the content of which is hereby incorporated by reference in its entirety. In an aspect, the agronomic gene may include an enzyme responsible for a hyper accumulation of a monterpene, a sesquiterpene, a steroid, hydroxamic acid, a phenylpropanoid derivative or another non-protein molecule with insecticidal activity.

In an aspect, the agronomic gene may include an enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic as described, by way of non-limiting example, in PCT Published Application No. WO93/02197, the content of which is hereby incorporated by reference in its entirety. DNA molecules which contain chitinase-encoding sequences can be obtained, for example, from the ATCC under Accession Nos. 39637 and 67152. Other DNA molecules encoding other biologically active molecules are described in, by way of non-limiting examples, Kramer et al., Insect Biochem. Molec. Biol. 23:691 (1993) and Kawalleck et al., Plant Molec. Biol.

21:673 (1993), wherein the content of each is incorporated by reference herein in its entirety.

In an aspect, the agronomic gene may include a molecule that stimulates signal transduction as described, by way of non-limiting example, in Botella et al., Plant Molec. Biol. 24:757 (1994) and Griess et al., Plant Physiol. 104:1467 (1994), wherein the content of each is incorporated by reference herein in its entirety. In an aspect, the agronomic gene may include a hydrophobic moment peptide, as described in PCT Published Application Nos. WO95/16776 and WO95/18855, wherein the content of each is incorporated by reference herein in its entirety.

In an aspect, the agronomic gene may include a membrane permease, a channel former or a channel blocker, as is described, by way of non-limiting example, in Jaynes et al., Plant Sci 89:43 (1993), the content of which is incorporated by reference herein in its entirety. In an aspect, the agronomic gene may include a viral-invasive protein or a complex toxin derived therefrom. By way of non-limiting example, the agronomic gene may be a viral coat protein imparting resistance to viral infection and/or disease development effected by the virus from which the coat protein gene is derived, as is described in Beachy et al., Ann. rev. Phytopathol. 28:451 (1990), the content of which is incorporated by reference herein in its entirety.

In an aspect, the agronomic gene may include an insect-specific antibody or an immunotoxin derived therefrom. By way of non-limiting example, an antibody targeted to a critical metabolic function in the insect gut would inactivate an affected enzyme, killing the insect, as described in C. F. Taylor et al., Abstract #497, Seventh Int'l Symposium on Molecular Plant-Microbe Interactions (Edinburgh, Scotland) (1994), the content of which is incorporated by reference herein in its entirety. In an aspect, the agronomic gene may include a virus-specific antibody as described, by way of non-limiting example, in Tavladoraki et al., Nature 366:469 (1993), the content of which is incorporated by reference herein in its entirety.

In an aspect, the agronomic gene may include a developmental-arrestive protein produced in nature by a pathogen or a parasite. By way of non-limiting example. a, fungal endo α-1,4-D-polygalacturonases may facilitate fungal colonization and plant nutrient release by solubilizing plant cell wall homo-α-1,4-D-galacturonase as is described in Lamb et al., Bio/Technology 10:1436 (1992) and Toubart et al., Plant J. 2:367 (1992), wherein the content of each is incorporated by reference herein in its entirety. In an aspect, the agronomic gene may include a development-arrestive protein produced in nature by a plant as described, by way of non-limiting example, in Logemann et al., BioTechnology 10:305 (1992), the content of which is incorporated by reference herein in its entirety.

In an aspect, the agronomic gene may include a herbicide that inhibits the growing point or meristem, such as an imidazalinone or a sulfonylurea. Non-limiting examples. of genes in this category code for mutant ALS and AHAS enzyme as described, for example, by Lee et al., EMBO J. 7:1241 (1988), and Miki et al., Theor. Appl. Genet 80:449 (1990), wherein the content of each is incorporated by reference herein in its entirety.

In an aspect, the agronomic gene may include genes imparting glyphosate resistance including, but not limited to, an EPSP gene which can confer glyphosate resistance as described in U.S. Pat. No. 4,940,835, a mutant aroA gene obtained under ATCC accession number 39256 and described in U.S. Pat. No. 4,769,061, glutamine synthetase genes described in EP Application No. 0333033 and U.S. Pat. No. 4,975,374, a phosphinothricin-acetyltransferase gene described in EP Application No. 0242246 and DeGreef et al., Bio/Technology 7:61 (1989), wherein the content of each is incorporated by reference herein in its entirety. Exemplary of genes conferring resistance to phenoxy propionic acids and cycloshexones, such as sethoxydim and haloxyfop are the Acc1-S1, Acc1-S2 and Acc1-S3 genes described by Marshall et al., Theor. Appl. Genet. 83:435 (1992), the content of which is incorporated by reference herein in its entirety.

In various other aspects, the agronomic gene may include at least one gene that confers or contributes to a value-added trait. In an aspect, the agronomic gene may include a gene that modifies fatty acid metabolism, including, but not limited to, an antisense gene of stearyl-ACP desaturase to increase stearic acid content of the plant, as described in Knultzon et al., Proc. Natl. Acad. Sci. U.S.A. 89:2624 (1992) the content of which is incorporated by reference herein in its entirety. In an aspect, the agronomic gene may include genes regulating phytate content, including a phytase-encoding gene configured to enhance breakdown of phytate, adding more free phosphate to the transformed plant, as described in Van Hartingsveldt et al., Gene 127:87 (1993), or a gene configured to reduce phytate content as described in Raboy et al., Maydica 35:383 (1990), wherein the content of each is incorporated by reference herein in its entirety. In an aspect, the agronomic gene may include a gene for modifying carbohydrate composition including, but not limited to, an enzyme that alters the branching pattern of starch as described in Shiroza et al., J. Bacteol. 170:810 (1988), Steinmetz et al., Mol. Gen. Genet. 20:220 (1985), Pen et al., Bio/Technology 10:292 (1992), Elliot et al., Plant Molec. Biol. 21:515 (1993), Søgaard et al., J. Biol. Chem. 268:22480 (1993), and Fisher et al., Plant Physiol. 102:1045 (1993), wherein the content of each is incorporated by reference herein in its entirety.

Any method for transforming the corn plants known in the art may be used to introduce one or more of the genes described above without limitation. Numerous methods for plant transformation have been developed, including biological and physical, plant transformation protocols. In an aspect, the corn plants may be transformed using the method described in Miki et al., Methods in Plant Molecular Biology and Biotechnology, Glick B. R. and Thompson, J. E. Eds. (CRC Press, Inc., Boca Raton, 1993) pages 67-88. In addition, expression vectors and in vitro culture methods for plant cell or tissue transformation and regeneration of plants may be used, as described in Gruber et al., "Vectors for Plant Transformation" in Methods in Plant Molecular Biology and Biotechnology, Glick B. R. and Thompson, J. E. Eds. (CRC Press, Inc., Boca Raton, 1993) pages 89-119, wherein the content of each is incorporated by reference herein in its entirety.

In an aspect, a method for introducing an expression vector into plants is based on the natural transformation system of *Agrobacterium* as described, by way of non-limiting example, in Horsch et al., Science 227:1229 (1985), the content of which is incorporated by reference herein in its entirety. In this aspect, Ti and Ri plasmids of *A. tumefaciens* and *A. rhizogenes*, respectively, carry genes responsible for genetic transformation of the plant, as described, by way of non-limiting example, in Kado, C. I., Crit. Rev. Plant Sci. 10:1 (1991)), the content of which is incorporated by reference herein in its entirety. Descriptions of *Agrobacterium* vector systems and methods for *Agrobacterium*-mediated gene transfer are described, by way of non-limiting example, in Moloney et al., Plant Cell Reports 8:238 (1989), and U.S. Pat. No. 5,591,616, wherein the content of each is incorporated by reference herein in its entirety.

In another aspect, a method for introducing an expression vector into plants is based on direct gene transfer methods. Despite the fact the host range for *Agrobacterium*-mediated transformation is broad, some major cereal crop species and gymnosperms have generally been recalcitrant to this mode of gene transfer, even though some success has recently been achieved in rice and corn. Several methods of plant transformation, collectively referred to as direct gene transfer, have been developed as an alternative to *Agrobacterium*-mediated transformation.

In one aspect. a generally applicable method of plant transformation is microprojectile-mediated transformation, in which DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Non-limiting examples of microprojectile-mediated transformation methods are described in Sanford et al., Part. Sci. Technol. 5:27 (1987), Sanford, J. C., Trends Biotech. 6:299 (1988), Klein et al., Bio/Technology 6:559-563 (1988), Sanford, J. C., Physiol Plant 7:206 (1990), and Klein et al., Biotechnology 10:268 (1992), wherein the content of each is incorporated by reference herein in its entirety. In corn, several target tissues can be bombarded with DNA-coated microprojectiles in order to produce transgenic plants, including, for example, callus (Type I or Type II), immature embryos, and meristematic tissue, in various aspects. Another method for physical delivery of DNA to plants is sonication of target cells as described in Zhang et al., Bio/Technology 9:996 (1991), the content of which is incorporated by reference herein in its entirety. Alternatively, liposome or spheroplast fusion may be used to introduce expression vectors into plants as described in Deshayes et al., EMBO J., 4:2731 (1985) and Christou et al., Proc Natl. Acad. Sci. U.S.A. 84:3962 (1987), wherein the content of each is incorporated by reference herein in its entirety. Direct uptake of DNA into protoplasts using $CaCl_2$ precipitation, polyvinyl alcohol or poly-L-omithine may be used to introduce expression vectors into plants as described in Hain et al., Mol. Gen. Genet. 199:161 (1985) and Draper et al., Plant Cell Physiol. 23:451 (1982), wherein the content of each is incorporated by reference herein in its entirety. In various additional aspects, electroporation of protoplasts and whole cells and tissues may be used to introduce expression vectors into plants as described in Donn et al., In Abstracts of VIIth International Congress on Plant Cell and Tissue Culture IAPTC, A2-38, p 53 (1990), D'Halluin et al., Plant Cell 4:1495-1505 (1992), and Spencer et al., Plant Mol. Biol. 24:51-61 (1994), wherein the content of each is incorporated by reference herein in its entirety.

Following transformation of corn target tissues, expression of the above-described selectable marker genes may be used for preferential selection of transformed cells, tissues and/or plants, using regeneration and selection methods well known in the art.

In various additional aspects, the foregoing methods for transformation may be used to produce a transgenic inbred line. This transgenic inbred line may then be crossed, with another (non-transformed or transformed) inbred line, in order to produce a new transgenic inbred line. Alternatively, a genetic trait which has been engineered into a particular corn line using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

"Inbred corn plant", as used herein, may include any single gene conversions of that inbred. The term single gene converted plant as used herein, refers to those corn plants developed by backcrossing as described herein, wherein essentially all of the desired morphological and physiological characteristics of an inbred are recovered in addition to the single gene transferred into the inbred via the backcrossing technique. Backcrossing methods can be used with the present disclosure to improve or introduce a characteristic into the inbred. The term backcrossing as used herein refers to the repeated crossing of a hybrid progeny back to one of the parental corn plants for that inbred. The parental corn plant which contributes the gene for the desired characteristic is termed the nonrecurrent or donor parent. This terminology refers to the fact that the nonrecurrent parent is used one time in the backcross protocol and therefore does not recur. The parental corn plant to which the gene or genes from the nonrecurrent parent are transferred is known as the recurrent parent as it is used for several rounds in the backcrossing protocol. In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a corn plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited to, male sterility, waxy starch, herbicide resistance, resistance for bacterial, fungal, or viral disease, insect resistance, male fertility, enhanced nutritional quality, industrial usage, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference in their entirety.

What is claimed is:

1. A seed of a corn inbred line designated MDS2713, representative seeds of the line having been deposited under ATCC Accession No. PTA-127082.

2. A corn plant, or a part thereof, produced by growing the seed of claim 1.

3. The corn plant, or a part thereof, of claim 2, wherein the part is selected from the group consisting of pollen, an ovule, a tissue culture of regenerable cells or protoplasts, or any combination thereof.

4. A corn plant, or a part thereof, having all of the physiological and morphological characteristics of the corn plant of claim 2.

5. A tissue culture of cells produced from the plant or a part thereof of claim 3, wherein the regenerable cells or protoplasts of the tissue culture are isolated from a tissue selected from the group consisting of meristemic cells, leaves, pollen, embryos, immature embryos, immature tassels, microspores, roots, root tips, anthers, silks, flowers, kernels, ears, cobs, husks, and stalks.

6. A corn plant regenerated from the tissue culture of claim 5, wherein the regenerated plant is capable of expressing all the morphological and physiological characteristics of inbred line MDS2713, representative seeds of the line having been deposited under ATCC Accession No. PTA-127082.

7. The corn plant, or a part thereof, of claim 4, wherein the corn plant is produced by a tissue culture process using the corn plant of inbred line designated MDS2713 as a starting material, representative seeds of the line having been deposited under ATCC Accession No. PTA-127082.

8. A method of producing a hybrid corn seed, the method comprising:
   (a) planting, in pollinating proximity, seeds of corn inbred lines MDS2713, representative seeds of the line having been deposited under ATCC Accession No. PTA-127082, and another corn inbred line;
   (b) inducing a lack of pollen production by plants of one of the corn inbred lines;
   (c) allowing natural cross-pollinating to occur between the plants of the corn inbred lines; and
   (d) harvesting the hybrid corn seed produced on cross-pollinated plants of the corn inbred lines.

9. An F1 hybrid corn seed produced by the method of claim 8.

10. A hybrid corn seed produced by a hybrid combination of plants of the corn inbred line designated MDS2713 of claim 1 and plants of another corn inbred line.

11. A hybrid corn plant grown from the hybrid corn seed of claim 10.

12. A tissue culture of the regenerable cells of the hybrid plant of claim 11.

13. A method for producing an herbicide resistant, insect resistant, or disease resistant corn plant comprising transforming the corn plant of claim 2 with a transgene that confers herbicide resistance, insect resistance, or disease resistance.

14. An herbicide resistant, insect resistant, or disease resistant corn plant produced by the method of claim 13.

15. A method of producing a corn plant with decreased phytate content, modified fatty acid metabolism, modified carbohydrate metabolism, and any combination thereof, comprising transforming the corn plant of claim 2 with one or more transgene encoding phytase, stearyl-ACP desaturase, fructosyltransferase, levansucrase, alpha-amylase, invertase, or starch branching enzyme.

16. A corn plant with decreased phytate content, modified fatty acid metabolism, modified carbohydrate metabolism, or any combination thereof, produced by the method of claim 15.

17. A method of producing a male-sterile corn plant comprising transforming the corn plant of claim 2 with a transgene that confers male sterility.

18. A male-sterile corn plant produced by the method of claim 17.

* * * * *